United States Patent [19]

Marks et al.

[11] Patent Number: 5,043,453
[45] Date of Patent: Aug. 27, 1991

[54] METHOD FOR HYDROAMINATING OLEFINS

[75] Inventors: Tobin J. Marks; Michel R. Gagne, both of Evanston, Ill.

[73] Assignee: Northwestern University, Evanston, Ill.

[21] Appl. No.: 482,296

[22] Filed: Feb. 20, 1990

Related U.S. Application Data

[63] Continuation of Ser. No. 291,186, Dec. 28, 1989, abandoned.

[51] Int. Cl.[5] .................. C07D 277/04; C07D 209/04
[52] U.S. Cl. .................................. 548/185; 548/400; 548/469
[58] Field of Search .................. 548/185, 400, 469

[56] References Cited

U.S. PATENT DOCUMENTS

| 29,368 | 10/1977 | Pez | 260/429.3 |
|---|---|---|---|
| 2,831,880 | 11/1958 | Benkeser | 260/439 |
| 3,060,215 | 1/1962 | Rosenberg et al. | 260/439 |
| 3,849,459 | 7/1974 | Maitlis et al. | 260/429 |
| 3,969,386 | 10/1976 | Ballard et al. | 260/429 |
| 4,423,276 | 4/1983 | Johnson | 585/665 |
| 4,665,046 | 3/1987 | Campbell, Jr. | 502/102 |
| 4,668,773 | 1/1987 | Marks et al. | 534/15 |
| 4,716,257 | 6/1987 | Marks et al. | 585/275 |
| 4,801,666 | 8/1989 | Marks et al. | 526/123 |

OTHER PUBLICATIONS

Watson, et al., "Homogeneous Lanthanide Complexes as Polymerization and Oligomerization Catalysts: Mechanistic Studies", ACS Symposium SEries, 1983, 212, 459–479.

Watson and Parshall, "Organolanthanides in Catalysis", Acc. Chem. Res., 1985, 18, 51–56.

Mauermann, Swepston, and Marks, "5f[3] vs. 4f[3]. Routes to and Properties of Highly Reactive Neodymium (III) Hydrocarbyl and Hydride Complexes", Organometallics, 4, 200, (1985).

Jeske, Schock, Swepston, Schumann, and Marks, "Highly Reactive Organolanthanides. Synthesis, Chemistry, and Structures of 4f Hydrocarbyls and Hydrides with Chelating Bis(polymethylcyclopentadienyl Ligands", J. Am. Chem. Soc., 1985, 107, 8103–8110.

Jeske, Lauke, Mauermann, Swepston, Schumann, and Marks, "Highly Reactive Organolanthanides, Systematic Routes to and Olefin Chemistry of Early and Late Bis(pentamethylcyclopentadienyl) 4f Hydrocarbyl and Hydride Complexes", J. Am. Chem. Soc., 1985, 107, 8091–8103.

Jeske, Lauke, mauermann, Schumann, and Marks, "Highly Reactive Organolanthanides. A Mechanistic Study of Catalytic Olefin Hydrogenation by Bis (pentamethylcyclopentadienyl) and Related 4F Complexes", J. Am. Chem. Soc., 1985, 107, 8111–8118.

Evans, et al., "Organolanthanide Hydride Chemistry. 3. Reactivity of Low-Valent Samarium with Unsaturated Hydrocarbons Leading to a Structurally Characterized Samarium Hydride Comples[1]", J. Am. Chem. Soc., 1983, 105, 1401–1403.

Deeba, et al., "Direct Amination of Ethylene by Zeolite Catalysis", J. Chem. Soc. Chem. Commun., 1987, 562–563.

Evans, William J., "Polyhedron Report Number 20: The Organometallic Chemistry of the Lanthanide Elements in Low Oxidation States", Polyhedron, 1987, vol. 6, No. 5, 803–835.

Finke, et al., "Organolanthanide and Organoactinide Oxidative Additons Exhibiting Enhanced Reactivity. 4. Products, Stoichiometry, and Preliminary Kinetic Studies of the Reaction of $(C_5Me_5)_2Sm^{II}OEt_2$ and $(C_5Me_5)_2Eu^{II}OEt_2$ with Alkyl and Aryl Halides. Evidence of Importance of Electron Transfer in Atom–Abstraction Oxidative Additions", Organometallics, 1987, 6, 1356–1358.

Hegedus et al., "palladium-Assisted Amination of Olefins. A Mechanistic Study", J. Am. Chem. Soc. 1984, 106, 7122–7126.

Surzur et al., "Bicyclisations Radicalaires Des N--Chloroamines Ethyleniques", Tetrahedron Letters, 1974, No. 25, 2191–2194.

Ambuehl et al., "Paltinum-Promoted Cyclization Reactions of Amino-Olefins. I. The Cyclization of 4-Aminopentene and Related Compounds", Journal of Organometallic Chemistry, 160 (1978), 329–335.

Fagan et al., "Insertion of Carbon Monoxide into Metal-Nitrogen Bonds, Synthesis, Chemistry, Structures, and Structural Dynamics of Bis(pentamethylcyclopentadienyl) Organoactinide Dialkylamides and $\eta^2$--Carbamoyls", J. Am. Chem. Soc., 1981, 103, 2206–2220.

Tamaru et al., "Urea as the Most Reactive and Versatile Nitrogen Nucleophile for the Palladium (2+)-Catalyzed Cyclization of Unsaturated Amines", J. Am. Chem. Soc., 1988, 110, 3994–4002.

Pez et al., "Metal Amide Catalyzed Amination of Olefins", Pure & Appl. Chem., 1985, vol. 57, No. 12, 1917–1926.

Pugin et al., "Palladium-Promoted Cyclization Reactions of Aminoalkenes", Journal of Organometallic Chemistry, 1981, 214, 125–133.

Gasc et al., "Tetrahedron Report No. 144: Amination of Alkenes", Tetrahedron, 1983, vol. 39, No. 5, 703–731.

Deeba et al., "Heterogeneous Acid–Catalyzed Amination of Isobutene to tert-Butylamine", J. Org. Chem., 1988, 53, 4594–4596.

*Primary Examiner*—Mary C. Lee
*Assistant Examiner*—Joseph K. McKane
*Attorney, Agent, or Firm*—Welsh & Katz, Ltd.

[57] ABSTRACT

The reaction of the organolanthanide complexes $([\eta^5-(CH_3)_5C_5]_2MH)_2$, (M being a lanthanide element) with amino-olefins provides a straight-forward route to a heterocyclic compound. Alternatively, the reaction of olefins with the organolanthanide complex in the presence of an amine results in an aminoalkane.

28 Claims, No Drawings

METHOD FOR HYDROAMINATING OLEFINS

This is a continuation of application Ser. No. 291,186, filed Dec. 28, 1989, now abandoned.

This application relates to catalysts and more particularly to a method for the hydroamination of olefins through the use of organolanthanide catalysts.

BACKGROUND OF THE INVENTION

The catalytic addition of N-H bonds to olefins (eq.(I)) to yield amines is a process of potentially great technological importance

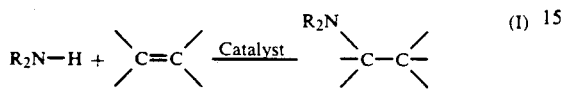 (I)

However, presently known catalyst systems, employing palladium, platinum, or alkali metal catalysts, can be relatively inefficient, having very low rates, poor catalyst lifetimes, poor selectivities, or requiring initial modification of the amine—e.g., tosylation. As a result, many current catalytic processes involve the conversion of alcohols to amines with the alcohol, which in turn, is prepared from the olefin Such hydroamination reactions are exothermic, yet thus far have proven difficult to perform due to a lack of suitable catalysts and, to a lesser extent, unfavorable entropy effects As a result, more attention has been paid to aminating olefins intramolecularly, and limited successes have been experienced in both stoichiometric and catalytic type reactions A rapid efficient, direct process for the hydroamination of olefins would be beneficial.

Organolanthanide catalysts have been found useful as noted in U.S. Pat. No. 4,668,773 to Marks and Mauermann; The organolanthanide complexes $[\eta^5-(CH_3)_5C_5]_2MCL_2-Li[(C_2H_5)_2O]2^+$, M=La, Nd, Sm, Lu, with $LiCH[Si(CH_3)_3]_2$ were shown to provide a straight-forward route to ether-free and halide-free bis(pentamethylcyclopentadienyl) lanthanide alkyls $[\eta^5(CH_3)_5C_5]_2MCH$ $[Si(CH_3)_3]_2$. Such $[\eta^5(CH_3)_5C_5]_2MCH[Si(CH_3)_3]_2$ complexes react with $H_2$ under mild conditions to yield the corresponding hydrides $[\eta^5(CH_3)_5(C_5)_2MH]_2$. These complexes have been found to be extremely active homogeneous olefin polymerization catalysts, as well as catalysts for olefin and acetylene hydrogenation.

SUMMARY OF THE INVENTION

Therefore, an object of the subject invention is the use of organolanthanide catalysts for use in hydroamination reactions.

Another object of the subject invention is a shelf-stable environmentally acceptable organolanthanide catalyst and its use in a method for the hydroamination of olefins.

A further object of the subject application is a method for the synthesis of heterocycle compounds from amino-olefins and aminocycloalkenes through hydroamination.

These and other objects are attained in accordance with the subject invention wherein organolanthanide catalysts are used as highly active catalysts for the hydroamination of olefins. In a first embodiment, α-amino olefins are utilized with an organolanthanide catalyst to form a heterocyclic compound. Amino cycloalkenes may also be utilized, providing steric hindrances are not too great. Organolanthanide catalysts such as those disclosed in U.S. Pat. No. 4,668,773, i.e., $R_2MR'$ where R=an alkyl, aryl, amido, or organometalloid group; R'=an alkyl group or hydrogen and M=a lanthanide series element, i.e., La, Ce, Pr, Nd, Pm, Sm, Ea, Gd, Tb, Dy, Ho, Er, Tm, Yb, and Lu; M may also be Yttrium, primarily in view of its similar properties. Equation II illustrates one example of a reaction cycle with a pentamethylcyclopentadienyl $((CH_3)_5C_5=Cp')$ lanthanum catalyst and an amino α-olefin. The first step (i) comprises the insertion of the α-olefin into the metal-nitrogen (M—N) bond. The second step (ii) is the protonolysis of the (metal-carbon (M—C) bond to release the heterocyclic product and regenerate the metal amide. This simple, efficient, and direct process results in the facile synthesis of a variety of heterocyclic compounds. The same general mechanism can be useful in forming alkylamines.

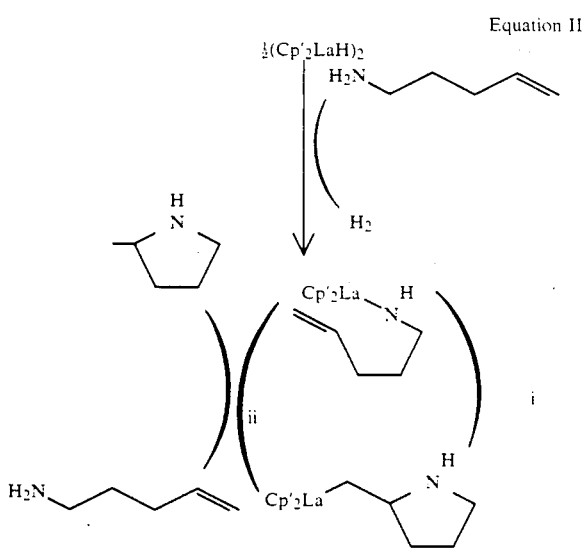

Equation II

In a second embodiment, all other amino olefins may be reacted with an organolanthanide catalyst to result in a heterocycle; here the amino olefin should not be of a structure as would sterically hinder the reaction.

In yet another embodiment of the invention, aminoalkanes can be synthesized by stirring solutions of an α-olefin or other non-sterically hindered olefin under an ammonia or other amine atmosphere or solution with an organolanthanide catalyst ($R_2MR'$) present.

DETAILED DESCRIPTION OF THE INVENTION

All operations were performed with rigorous exclusion of oxygen and moisture in flamed Schlenk-type glassware in a dual manifold Schlenk line or interfaced to a high vacuum ($10^{-5}$ torr) system, or in a nitrogen or argon filled glovebox with a high capacity atmosphere recirculator. Argon, ethylene, propylene, dihydrogen, and deuterium gas were purified by passage through a supported MnO oxygen removal column and a molecular sieve column. Aliphatic hydrocarbon solvents were pretreated with concentrated $H_2SO_4$, $KMnO_4$ solution, $MgSO_4$, and Na+4A molecular sieves. All reaction solvents were distilled from Na/K/benzophenone under nitrogen and were condensed and stored in vacuo in bulbs on the vacuum line containing a small amount of [Ti($\eta^5$-C$_5$H$_5$)$_2$Cl]$_2$ZnCl$_2$ as indicator. Cyclohexane and heptane were additionally vacuum transferred onto Na/K and stirred for at least a day before use in catalytic experiments. The olefins, all hexenes, and cyclohexene were purified by stirring over Na/K for at least 6 hours and were freshly vacuum transferred. The amines were purified by stirring over Na/K for ½ hour, followed by at least 3 successive vacuum transfers onto freshly activated 4Å molecular sieves (at least 1 day each); and freshly vacuum transferred before use. Deuterated solvents were dried over Na/K and vacuum transferred before use.

Anhydrous lanthanide halides were prepared from the corresponding oxide and ammonium chloride. Pentamethylcyclopentadiene was prepared by the procedure set forth in *Organometallics*, 1984, 3, 819-821. The complexes Cp'$_2$NdCl$_2$—Li((C$_2$H$_5$)$_2$O)$_2^+$ and Cp'$_2$LuCl$_2$—Li((C$_2$H$_5$)$_2$O)$_2^+$ were prepared as known in the art. Bis(trimethylsilyl)methyllithium (LiCHTMS$_2$) and 2-lithium-mesitylene were also prepared as known in the art.

I. Catalyst Syntheses

In general, Cp'$_2$MCHTMS$_2$ and 2-(Cp'$_2$M)mesitylene may be prepared by mixing approximately equimolar amounts of Cp'$_2$MCl$_2$Li(C$_2$H$_5$)$_2$O)$_2$' and LiCHTMS$_2$ or 2-lithium-mesitylene, as appropriate, in toluene for 8-16 hours (preferably 12 hours) and −10° C. to 25° C. (preferably 0° C.). The solvent is then removed and the residue extracted with another solvent, preferably pentane. The extract is cooled to recrystallize the Cp'$_2$MCHTMS$_2$ or 2-(Cp'$_2$M)mesitylene.

EXAMPLE 1

Cp'$_2$LaCl$_2$—Li((C$_2$H$_5$)$_2$O)$_2^+$

A suspension of 2.1 g (8.6 mmol) anhydrous LaCl$_3$ and 2.44 g (17.2 mmol) LiCp' in 120 ml THF was refluxed for 12 hours at 0° C. The solvent was then removed in vacuo, being careful to keep the temperature below 10° C. to avoid formation of a less reactive complex (probably (Cp'$_2$LaCl)$_2$). The white residue was then extracted with 200 mL diethyl ether, the mixture filtered, reduced in volume to 30 mL, and slowly cooled to −30° C. Decantation of the solvent and drying under high vacuum yielded 2.7 g (49.4%) of Cp'$_2$LaCl$_2$—Li((C$_2$H$_5$)$_2$O)$_2^+$ as a white, microcrystalline solid. Additional product can be obtained from the mother liquor.

EXAMPLE 2

Cp'$_2$LaCHTMS$_2$

A suspension of 2.6 g (4.11 mmol) Cp'$_2$LaCl$_2$-Li((C$_2$H$_5$)$_2$O)$_2^+$ and 0.68 g (4.1 mmol) LiCH(TMS)$_2$ in 150 mL toluene was stirred for 12 hours at 0° C. The solvent was then removed in vacuo and the white residue extracted with 100 mL pentane. The resulting mixture was then filtered, the volume of the filtrate reduced to 30 mL, and the filtrate slowly cooled to −30° C. Pale yellow crystals of Cp'$_2$LaCH(TMS)$_2$ were isolated by decantation and subsequent vacuum drying. Yield: 1.4 g (60%)

EXAMPLE 3

Cp'$_2$NdCH(TMS)$_2$

The above procedure set forth in Examples 1 and 2 was repeated with 5.1 g (8.0 mmol) Cp'$_2$NdCl$_2$—Li((C$_2$H$_5$)$_2$O)$_2^+$·and 1.32 g (8.0 mmol) LiCH(TMS)$_2$ in 50 mL toluene to yield, after work-up and recrystallization from pentane, 3.67 g (80%) of Cp'$_2$NdCH(TMS)$_2$ as blue-green crystals.

EXAMPLE 4

Cp'$_2$SmCHTMS$_2$ (One-pot procedure)

A mixture of 1.00 g (3.90 mmol) SmCl$_3$ and 1.11 g (7.79 mmol) LiCp' was refluxed in 50 mL THF for 8 hours at 60° C. The solvent was then removed in vacuo and the residue, together with 0.65 g (3.94 mmol) LiCH(TMS)$_2$, was suspended in 50mL toluene at −78° C. The mixture was allowed to gradually warm to room temperature over the next 12 hours, the solvent removed under high vacuum, and the residue extracted with 50mL pentane. Subsequent filtration, slow cooling of the filtrate to −78° C., filtration and drying produced 0.600 g (27%) of Cp'$_2$SmCH(TMS)$_2$ as red-brown crystals. An additional 0.400 g (18%) of product can be recovered from the mother liquor (total yield=45%).

EXAMPLE 5

Cp'$_2$LuCH(TMS)$_2$

The aforementioned procedure set forth in Example 4 for Cp'$_2$LaCH(TMS)$_2$ was carried out with 3.1 g (4.62 mmol) Cp'$_2$LuCl2-Li((C$_2$H$_5$)$_2$O)$_2^+$ and 0.79 g (4.7 mmol) LiCH(TMS)$_2$ in 150 mL of toluene. The standard workup and pentane recrystallization yielded 1.8 g (64%) of Cp'$_2$LuCH(TMS)$_2$ as colorless crystals.

(Cp'$_2$MH)$_2$ compounds may be prepared by stirring Cp'$_2$MCH(TMS)$_2$/pentane or 2-(Cp'$_2$M)mesitylene/-pentane under a hydrogen atmosphere for 0.1-1.5 hours (preferably 2 hours) at a temperature of −10° C. to 10° C. (preferably 0° C.). The resulting precipitate may be isolated by filtration, washing and the like.

EXAMPLE 6

(Cp'$_2$LaH)$_2$

Cp'$_2$LaCH(TMS)$_2$ (0.200 g, 0.35 mmol) was stirred under H$_2$ atmosphere in 50 mL of pentane for 2 hours at 0° C. The resulting colorless precipitate was isolated by filtration, washed with 2×3 mL pentane, and dried in vacuo to yield 0.14 g (98%)(Cp'$_2$LaH)$_2$ as a colorless, microcrystalline solid.

EXAMPLE 7

(Cp'$_2$NdH)$_2$

The above procedure set forth in Example 6 was carried out with 1.00 g (1.74 mmol) Cp'$_2$NdCH(TMS)$_2$ in 50 mL pentane. Filtration, washing, and drying yielded 0.600 g (83%) of (Cp'$_2$LaH)$_2$ as a blue-green, microcrystalline powder.

EXAMPLE 8

(Cp'$_2$SmH)$_2$

This compound was prepared from Cp'$_2$SmCH(TMS)$_2$ using the procedure above for (Cp'$_2$LaH)$_2$ set forth in Example 6 and was isolated as a pink powder.

EXAMPLE 9

(Cp'$_2$LuH)$_2$

This complex was prepared by the aforementioned procedure for (Cp'$_2$LaH)$_2$ as set forth in Example 6 using H$_2$ in pentane. The yield of (Cp'$_2$LuH)$_2$ was 98% colorless, polycrystalline solid.

II. Hydroamination

The anaerobic catalytic reaction of (Cp'$_2$LaH)$_2$ with a variety of dry, degassed amino olefins and alkenes (typically in 100-20-fold stoichiometric excess) proceeds to completion in hydrocarbon solvents such as toluene, cyclohexane, or pentane. The reactions may be conveniently monitored by NMR spectroscopy and the products may be identified by comparison with literature spectral data and/or with those of authentic samples.

By supplying olefins to the lanthanide-N bond intramolecularly in an organolanthanide compound, it is possible to have a large effective concentration of olefin around the amine, while at the same time reducing the disfavoring entropic factor referred to above when the reaction is performed intermolecularly.

A. Synthesis of Heterocycles

To investigate one aspect of olefin hydroamination and in furtherance of one embodiment of the subject invention, a variety of primary unsaturated amines were synthesized, as set forth in Examples 10 through 18 below which, when reacted with catalytic amounts of an organolanthanide catalyst, R$_2$MR', where R=an alkyl, aryl, amido, or organometalloid group; and R'=an alkyl group or hydrogen; and M is a lanthanide element or Yttrium. Examples of R$_2$MR' are (Cp'$_2$LaH)$_2$, (Cp'$_2$LuH)$_2$, or the organometalloid lanthanum catalyst Me$_2$SiCp''$_2$LuCH(TMS)$_2$Cp''=Me$_4$C$_5$; these catalysts readily give off H$_2$, forming the expected organolanthanide complexes. Such amido complexes all have the ability to intramolecularly insert an olefin into the lanthanide-NHR bond. The insertion results in an alkyl complex which, in the presence of excess amine, is rapidly protonated, yielding an alkane, and reforming an amido compound. The combination of all the reactions set forth in Equation II constitutes a catalytic cycle which demonstrates the key steps involved in forming a group of heterocyclic compounds. The number of such cycles which the catalyst can go through per unit time is known as the Turnover Frequency (N$_t$) and may be used to measure the efficiency of the catalyst, when considered with other factors.

EXAMPLE 10

5 mg (6.1 μmol) of (Cp'$_2$LaH)$_2$ is added to a reaction flask under a nitrogen atmosphere. The flask is connected to a high vacuum line, evacuated and 5 mL pentane is vacuum transferred to the reaction flask. 0.5 g (5.9 mmol) of 1-amino-4-pentene which has been rigorously dried and degassed is then vacuum transferred onto the catalyst. The reaction flask is sealed and the solution warmed to room temperature; once H$_2$ evolution ceases, the solution is warmed to 40° C. and stirred for 6 hours. The contents are then vacuum transferred to a second vessel. The solvent is removed on a rotoevaporator to yield the desired heterocycle. Analysis of the product may be performed by NMR as a manner known in the art.

Utilizing this method, a number of heterocycles can be synthesized as shown in Table I. Turnover frequencies (N$_t$) may then be calculated using standard NMR techniques. The turnover frequency shows a dependence on the size of the metal; this is shown very dramatically in Examples 12 and 14, and reflects increased crowding in the transition state associated with the turnover limiting olefin insertion as one regresses in size and with increasing atomic number from La to Lu.

TABLE I

| Example | Starting Amine | Product | Catalyst | N$_t$(hr$^{-1}$) | (Temp(°C.)) | Solvent |
|---|---|---|---|---|---|---|
| 10 | H$_2$N~~~= | H-N (pyrrolidine) | (Cp'$_2$LaH)$_2$ | 13 | 25 | Toluene |
| 11 | H$_2$N~~~~= | H-N (piperidine) | (Cp'$_2$LaH)$_2$ | 140 | 60 | Cyclohexane |
| 12 | H$_2$N-C(Me)$_2$-CH$_2$-CH=CH$_2$ | H-N (gem-dimethyl pyrrolidine) | (Cp'$_2$LaH)$_2$ | 125 | 25 | Toluene |
| 13 | H$_2$N-C(Me)$_2$-CH$_2$-CH=CH$_2$ | H-N (gem-dimethyl pyrrolidine) | Me$_2$SiCp''$_2$LuCH(TMS)$_2$ | 75 | 80 | Toluene |
| 14 | H$_2$N-C(Me)$_2$-CH$_2$-CH=CH$_2$ | H-N (gem-dimethyl pyrrolidine) | (Cp'$_2$LuH)$_2$ | <1 | 80 | Toluene |
| 15 | NH$_2$-CH(Me)-CH$_2$CH$_2$-CH=CH$_2$ | H-N (methyl piperidine) | (Cp'$_2$LaH)$_2$ | 10 | 80 | Toluene |

TABLE I-continued

| Example | Starting Amine | Product | Catalyst | $N_t(hr^{-1})$ | (Temp(°C)) | Solvent |
| --- | --- | --- | --- | --- | --- | --- |
| 16 | $H_2N\diagup\diagdown\diagup\diagdown\diagup\diagdown$ | H-N-piperidinyl (2-methyl) | $(Cp'_2LaH)_2$ | 5 | 60 | Toluene |
| 17 | 2-allylaniline | 2-methylindoline | $(Cp'_2LaH)_2$ | 13 | 80 | Toluene |
| 18 | $D_2N\diagup C(CH_3)_2\diagup CH_2\diagup CH=CH_2$ | deuterated 2-methyl-5,5-dimethylpyrrolidine | $(Cp'_2LaH)_2$ | 25 | 26 | Toluene |

For a given amine, catalyst activities are generally observed to follow the same trends as propylene oligomerization by $R_2MR'$ complexes with the larger, lighter metals being fastest (La and Lu). Thus, $(Cp'_2LaH)_2 > [Me_2Si(Me_4C_5)_2LuH]_2 = [Me_2SiCp''_2LuH]_2 > (Cp'_2LuH)_2$ in order of catalytic activity. By varying the amine one can also see a number of points, the most noticeable being the regiospecificity of the cyclizations. In each case, it is possible to insert the olefin in one of two orientations, hypothetically yielding the following structures with 1-amino-4-pentene as the amine:

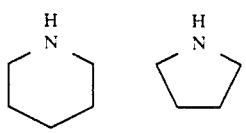

However, as is the case with 1-amino-4-pentene, and with the other amines, the smaller of the two possible ring sizes corresponding to lower ring strain in the transition state appears to be favored with no indication of any side products.

As set forth above, 5-membered rings (e.g., Example 10) are formed much more readily than the corresponding 6-membered rings. The fact that six membered rings can be formed at all is noteworthy since other systems appear to have trouble or will not cyclize unsubstituted piperidines. It was observed that the product of Example 12 is cyclized at a drastically increased rate over the product of Example 10. One theory suggests that the rate increase is due to the relief of steric congestion in the acyclic form of Example 14 relative to the cyclized amine. Examples 11 and 12 show that the turnover frequencies also appear independent of the choice of hydrocarbon solvent.

By studying the kinetics of this process, one sees that the rate of appearance of cyclized product and hence the disappearance of the starting amine is linear with time, indicating zero order kinetics in the substrate. In the catalytic cycle, there are only two steps involved in the process, and since it is known that amine protonolysis o lanthanide-alkyls is rapid, the rate determining step should be the olefin-insertion into the lanthanide-N bond, indicating a sterically controlled process. There is useful information in this observation, namely that if this system behaves as other organolanthanide catalysts, then by opening the coordination sphere of the catalyst, there should be a rate increase. This has indeed been the case; when the $(CH_3)_2Si[(CH_3)_4C_5]_2^{-2}$ ligand is used, one sees a turnover frequency increase of greater than an order of magnitude. Information which is consistent with the proposed mechanism can be obtained when the amine N,N-$d_2$-1-amino-2,2-dimethyl-4-pentene is used. In Example 18, the deuterium labels in the cyclized product are exclusively located in positions which can be predicted with Equation II via deuterolysis of the intermediate alkyl by $D_2NR$.

B. Synthesis of Aminoalkanes

In addition to synthesizing heterocycles through hydroamination, olefins, such as ethylene, propylene, butadiene, 1-butene, 1-hexene, 1,5-hexadiene, 1-heptene, and the like, can be hydroaminated with ammonia or other primary and secondary amines, such as $R''NH_2$, $R''_2NH$, where $R''$ can be an alkyl or aryl group. Hydroamination can be effected by stirring solutions of $R_2MR'$, such as $(Cp'_2LaH)_2$, under an ammonia atmosphere at various pressures. It is believed that most olefins can be hydroaminated provided that steric considerations are favorable and do not substantially impede the progress of the reaction. M could be any of the Lanthanide Series, including Yttrium, as set forth above. $(CH_3)_2SiCp''_2MCH(TMS)_2$ may also be used. The solvents involved are as before. This process presumably involves ammonia or $-NH_2$ at the insertion step, dependent on the amine source.

EXAMPLE 19

20 mg (24.4 μmol) of $(Cp'_2LaH)_2$ is added to a reaction flask under a nitrogen atmosphere. The flask is connected to a high vacuum line and evacuated. 2 g (24 mmol) of 1-hexene which has been rigorously dried and degassed is then vacuum transferred onto the catalyst with stirring, the solution is then put under an atmosphere of ammonia. Once $H_2$ evolution has ceased, the reaction is monitored by the ammonia uptake. Once ammonia uptake has ceased, the solution is degassed, and the contents are then vacuum transferred to a second vessel. The result is 2-amino-hexane.

In general, it should be noted that the overall catalytic mechanism is sensitive to Lewis Bases and Brönsted Acids. Therefore, if hydroamination of materials that contain alcohols, thiols, carboxylic acids, or the like is required, protecting groups may be needed and can therefore be added as known in the art to inhibit the effect the interfering groups may have.

C. Heterogeneous Catalysis

In addition to the homogeneous catalytic synthesis methods described above, heterogeneous catalytic synthesis methods are envisioned as being within the scope of the subject invention as well. In such a heterogeneous process, the organolanthanide catalyst would be absorbed on the surface of a suitable inorganic substrate such as silica, silica gel, alumina, magnesium chloride, magnesium oxide or the like, and placed in contact with the reactants.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A method for hydroaminating an amino-olefin, comprising contacting said amino-olefin with an organolanthanide catalyst under an inert atmosphere, said catalyst having the formula $R_2MR'$ where R is an alkyl, aryl, amido, or organometalloid group and R' is an alkyl group or hydrogen, and M is selected from the group consisting of La, Ce, Pr, Nd, Pm, Sm, Eu, Gd, Tb, Dy, Ho, Er, Tm, Yb, Lu, and Y.

2. A method for hydroaminating an amino-olefin, comprising contacting said amino-olefin with a catalyst under an inert atmosphere, said catalyst having a formula selected from the group consisting of $(Cp'_2MH)_2$ and Cp'' is $(CH_2)_4C_5$ $(CH_3)_2SiCp''_2MCH[Si(CH_3)_3]_2$, wherein Cp' is $\eta^5(CH_3)_5C_5$; and M is selected from the group consisting of La, Ce, Pr, Nd, Pm, Sm, Eu, Gd, Tb, Dy, Ho, Er, Tm, Yb, Lu, and Y, whereby a heterocycle is formed.

3. The method of claim 1 wherein said amino-olefin is selected from the group consisting of:

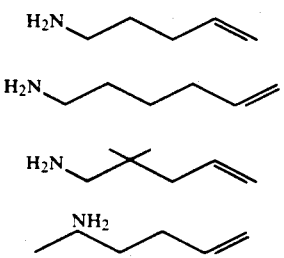

4. The method of claim 2 wherein said catalyst solution has a solvent selected from the group consisting of tetrahydrofuran, cyclohexane, toluene, benzene, and pentane.

5. The method of claim 2 wherein said catalyst is homogeneous.

6. The method of claim 2 wherein said catalyst is heterogeneous.

7. The method of claim 5 wherein said catalyst is adsorbed on an inorganic substrate selected from the group consisting of silica, silica gel, alumina, magnesium chloride, and magnesium oxide.

8. A method for hydroaminating an unsaturated monomer selected from the group consisting of amino-olefins and amino cycloalkenes comprising the steps of dissolving said unsaturated monomer in a solvent and contacting said olefin and solvent solution with a lanthanide catalyst of the formula $R_2MR'$ under an inert atmosphere wherein R is selected from the group consisting of alkyl, aryl, amido, and organometalloid group; R' is selected from the group consisting of an alkyl group, organometalloid group and hydrogen, and M is selected from the group consisting of the Lanthanide Series elements and Yttrium.

9. The method of claim 8 wherein said solvent is selected from the group consisting of aliphatic hydrocarbons, aromatic hydrocarbons, and mixtures thereof.

10. The method of claim 8 wherein said solvent is toluene.

11. The method of claim 8 wherein M is selected from the group of lanthanide elements consisting of La, Ce, Nd, and Sm.

12. The method of claim 8 wherein said unsaturated monomer is selected from the group consisting of:

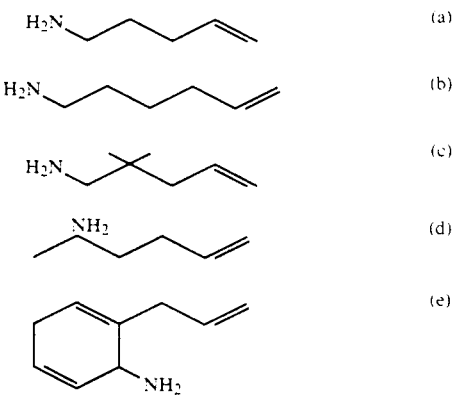

13. A method of hydroaminating an amino-olefin, comprising the steps of:
(a) evacuating a reaction vessel;
(b) adding a solvent to said reaction vessel;
(c) adding a catalyst solution containing an organolanthanide compound of the formula $R_2MR'$ where R is an alkyl, aryl, amido, or organometalloid group, and R' is an alkyl group, organo-metalloid group or hydrogen, and M is a lanthanide selected from the group consisting of: La, Ce, Pr, Nd, Pm, Sm, Ea, Gd, Tb, Dy, Ho, Er, Tm, Yb, Lu, and Y to said reaction vessel;
(d) maintaining pressure with an atmosphere selected from argon or nitrogen in said reaction vessel at approximately one atmosphere;
(e) stirring the solvent and catalyst solution rapidly for several minutes;
(f) transferring to said mixture an amino-olefin; and
(g) heating the reaction vessel, whereby the amino-olefin forms into a heterocyclic compound which may be isolated.

14. A method of claim 13 where $R_2MR'$ is selected from the group consisting of $(Cp'MH)_2$ and $(CH_3)_2SiCp''_2MCH[Si(CH_3)_3]_2$.

15. A method for hydroaminating an olefin, to form an aminoalkane comprising contacting said olefin with a catalyst in the presence of an amine selected from the group consisting of $NH_3$, $R''NH_2$, $R''_2NH$, where $R''$ is an alkyl or aryl group, said catalyst having the formula $R_2MR'$, where R is an alkyl, aryl, amido, or organometalloid; R' is an alkyl group, organo-metalloid group or hydrogen; and M is selected from the group consisting of La, Ce, Pr, Nd, Pm, Sm, Eu, Gd, Tb, Dy, Ho, Er, Tm, Yb, Lu, and Y.

16. The method of claim 15 wherein said olefin is selected from the group consisting of ethylene, propylene, 1-butene, butadiene, 1-hexene, 1-heptene, and 1,5-hexadiene.

17. The method of claim 15 wherein said catalyst solution has a solvent selected from the group consisting of tetrahydrofuran, cyclohexane, toluene, benzene, and pentane.

18. The method of claim 15 wherein said catalyst is homogeneous.

19. The method of claim 15 wherein said catalyst is heterogeneous.

20. The method of claim 15 wherein said catalyst is selected from the group consisting of $(Cp'_2MH)_2$ and $(CH_3)_2SiCp''_2MCH[Si(CH_3)_3]_2$.

21. The method of claim 19 wherein said catalyst is adsorbed on an inorganic substrate selected from the group consisting of silica, silica gel, alumina, magnesium chloride, and magnesium oxide.

22. A method for hydroaminating an unsaturated monomer selected from the group consisting of α-olefins and cycloalkenes comprising the steps of dissolving said unsaturated monomer in a solvent and contacting said olefin solution with a lanthanide catalyst of the formula $R_2MR'$ under an ammonia atmosphere wherein R is an alkyl, aryl, amido, or organometalloid group; R' is an alkyl or hydrogen; and M is selected from the group consisting of the Lanthanide Series elements and Yttrium.

23. The method of claim 22 wherein said solvent is selected from the group consisting of aliphatic hydrocarbons, aromatic hydrocarbons, and mixtures thereof.

24. The method of claim 22 wherein said solvent is toluene.

25. The method of claim 22 wherein M is selected from the group of lanthanide elements consisting of La, Nd, and Sm.

26. The method of claim 22 wherein said unsaturated monomer is selected from the group consisting of ethylene, propylene, 1-butene, butadiene, 1-hexene, 1,5-hexadiene, and 1-heptene.

27. The method of claim 22 wherein said catalyst comprises $[(\eta^5(CH_3)_5C_5)_2MH]_2$.

28. A method of hydroaminating an olefin, comprising the steps of:
  (a) evacuating a reaction vessel;
  (b) adding a solvent to said reaction vessel;
  (c) adding a catalyst solution containing an organolanthanide compound of the formula selected from the group consisting of $(Cp'_2MH)_2$ and $(CH_3)_2SiCp''_2MCH(CH_3)_3Si)_2$ where M is a lanthanide selected from the group consisting of: La, Ce, Pr, Nd, Pm, Sm, Ea, Gd, Tb, Dy, Ho, Er, Tm, Yb, Lu, and Y to said reaction vessel;
  (d) maintaining pressure with an atmosphere of ammonia in said reaction vessel at approximately one atmosphere;
  (e) stirring the solvent and catalyst solution rapidly for several minutes;
  (f) transferring to said mixture an olefin; and
  (g) heating the reaction vessel, whereby an amidoalkane is formed and may be isolated

* * * * *